US00PP14136P39

(12) United States Plant Patent
Hirabayashi

(10) Patent No.: US PP14,136 P3
(45) Date of Patent: Sep. 16, 2003

(54) PETUNIA PLANT NAMED 'KEIREOM'

(75) Inventor: Hiroshi Hirabayashi, deceased, late of Yachioyo (JP), by Eriko Hirabayashi, Minako Hirabayashi, Kanako Hirabayashi, legal representatives

(73) Assignee: Keisei Rose Nurseries, Inc., Tokyo (JP)

( * ) Notice: Subject to any disclaimer, the term of this patent is extended or adjusted under 35 U.S.C. 154(b) by 0 days.

(21) Appl. No.: 10/020,553

(22) Filed: Dec. 6, 2001

(65) Prior Publication Data

US 2003/0110546 P1 Jun. 12, 2003

(51) Int. Cl.[7] ..... A01H 5/00

(52) U.S. Cl. ..... Plt./356

(58) Field of Search ..... Plt./356

*Primary Examiner*—Bruce R. Campell

*Assistant Examiner*—Susan B. McCormick

(74) *Attorney, Agent, or Firm*—Klarquist Sparkman, LLP

(57) ABSTRACT

Petunia plant having profuse, bright red, medium sized flowers; and a pendant, free branching, vigorous growth habit.

2 Drawing Sheets

Genus and species: *Petunia×hybrida.*
Variety denomination: 'KEIREOM'.

SUMMARY OF THE INVENTION

The present invention relates to a new and distinct variety of petunia plant which was originated by me by crossing two unnamed varieties, neither of which are patented.

BACKGROUND OF THE INVENTION

The primary objective of this breeding was to produce a new petunia variety having bright red, medium sized single flowers; a free flowering, pendant habit and free branching.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Vigorous habit; and
2. Profuse flowering.

Asexual reproduction of this new variety by cuttings (roots in two weeks), as performed Yachigo-shi, Chiba-ken, Japan and at Somis, Calif., shows that the foregoing and all other characteristics and distinctions come true to form and are established and transmitted through succeeding propagations.

COMPARISON WITH SIMILAR VARIETY

KEIreom is similar in vigor, branching and growth habit to 'KEllavbu' (U.S. Plant Pat. No. 13,542), but 'KEIreom' has red flowers whereas 'KEllavbu' has blue flowers.

BRIEF DESCRIPTION OF THE ILLUSTRATIONS

In the attached photographs

Figure 1:
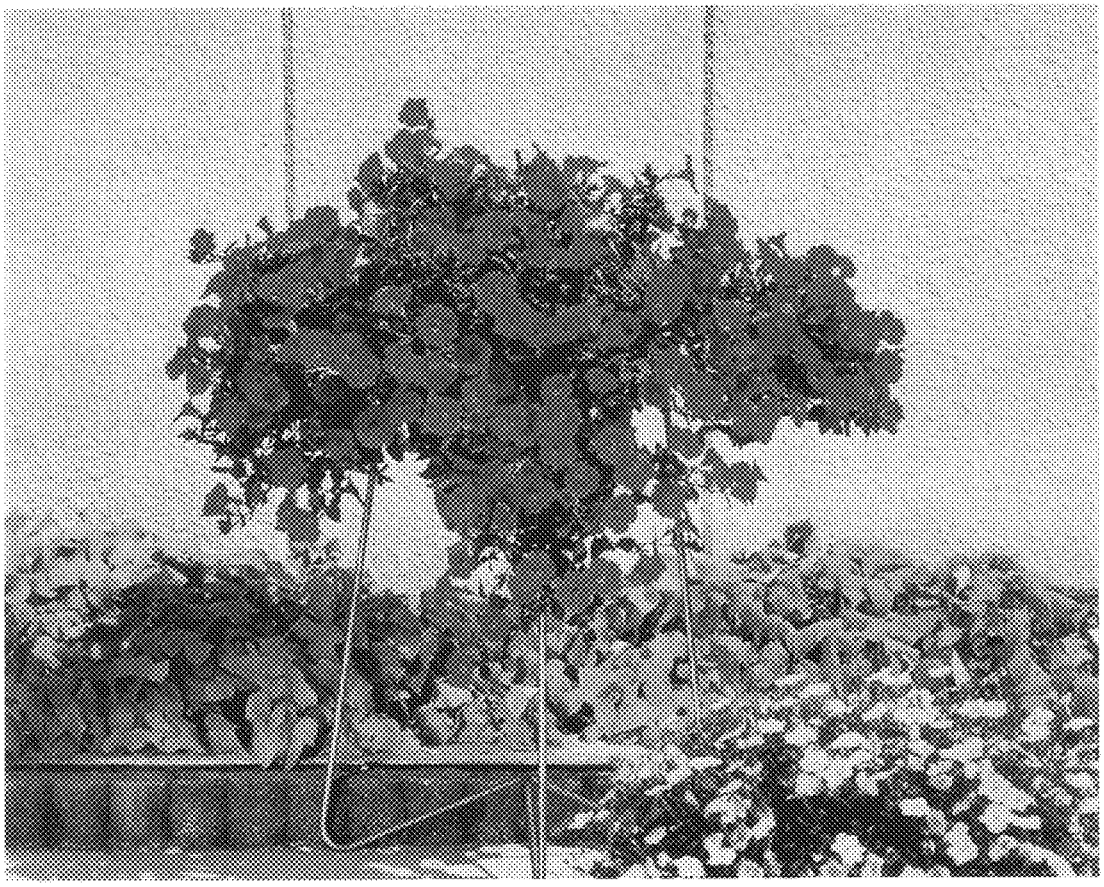
Figure 2:
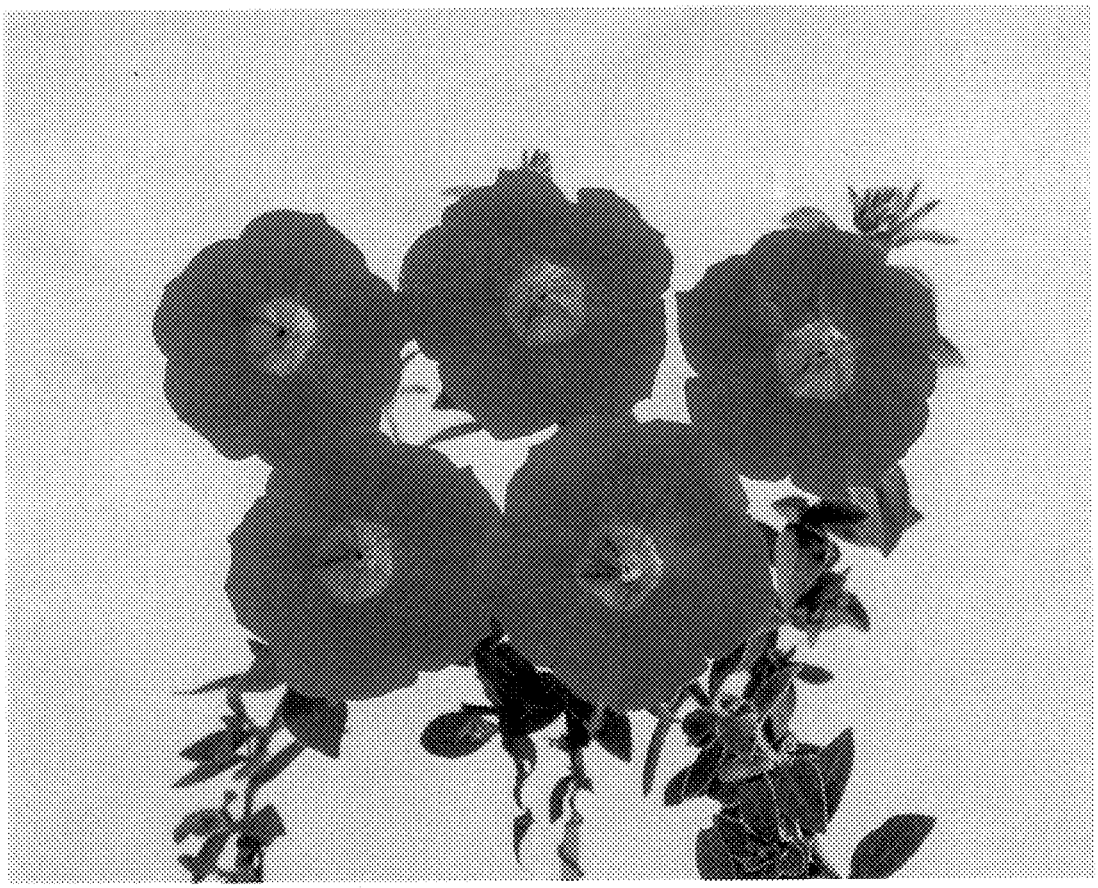

FIG. 1 is a view of the entire plant grown in a hanging pot in a garden environment, and FIG. 2 is an enlarged view of a portion of the plant showing several flowers and a portion of the foliage.

DETAILED BOTANICAL DESCRIPTION

The following is a detailed description of my new petunia cultivar with color descriptions using terminology in accordance with The Royal Horticultural Society (London) Colour Chart, except where ordinary dictionary significance of color is indicated.

Parentage:
*Seed parent.*—Unnamed seedling.
*Pollen parent.*—Unnamed seedling.

FLOWER

Observations made from 3-month old plants grown in a garden environment at Somis, Calif. January, 2001 to May, 2001.

Blooming habit: Continuous spring, summer and fall.
*Plant.*—
*Growth habit.*—Vigorous and spreading.
*Mature Plant.*—Height: 10 to 15 cm. Spread in diameter: 30–40 cm.
*Stem.*—Overall Length: 10 to 20 cm. Main Stem: 20 cm. Laterals: 8 to 10 cm. Thickness: 2.0 to 2.5 mm. Color: Yellow-Green Group 144A. (No anthocyanin pigmentation observed.) Pubescence: Pubescent. Mode of Branching: Abundant. Length of Internode: 1.0 to 2.0 cm.
*Leaf.*—Arrangement on stem: Horizontal. Phyllotaxis: Alternate. Overall Shape: Ovate. Apex Shape: Rounded. Base Shape: Rounded. Length: 3.0 to 5.5 cm. Width: 2.5 to 3.0 cm. Thickness: 0.4 mm. Petiole: Absent. Color: Upper surface: Yellow-Green Group 146A. Lower surface: Yellow-Green Group 146A. Pubescence: Pubescent. Variegation: None. Margin: Smooth. Venation Pattern: Costate. Color of Vein: Green Group 137C.

*Bud.*—Overall length: 40 mm just before unfolding. Color: Top 10 mm: Red Group 42C. Lower 30 mm: Greyed Purple Group 183D with a caste of Yellow-Green Group 147C.

Flower:

*Orientation of opening.*—Slantly upward.

*Size.*—Average open diameter is about 4.0 to 4.5 cm.

*Type.*—Single, fused petal.

*Shape of corolla tube.*—Funnel.

*Shape of flower.*—Funnel form, five lobed.

Petal:

*Color.*—The upper and lower sides of the petals shade from their outer tip from Red Group 45C, to 46C in middle portion and 47B at the innermost portion.

*Corolla tube.*—Inside surface: Bottom color: Greyed-White Group 156B and 156C. Outside surface: Green-Yellow Group 1D. Diameter: 4.0 to 4.5 cm. Length: 2.0 to 3.0 cm.

*Margin.*—Smooth.

*Length.*—40 mm.

*Tip shape.*—Entire.

*Lobation.*—Shallow.

*Waving.*—Weak.

*Peduncle.*—Length: 1.0 to 1.5 cm. Color: Yellow-Green Group 145B.

*Calyx.*—Number of sepals: Five. Length: 1.5 cm. Color: Yellow-Green Group 144A.

*Texture.*—Velutinous.

Reproductive parts:

*Anther.*—Color: Yellow-Green Group 153D.

*Filament.*—Color: Yellow-White Group 158D.

*Pistil.*—Quantity: One Color: Yellow-Green Group 154C. Length: 10–14 mm.

*Stamens.*—Quantity: Five. Length: 8–11 mm.

Disease resistance: Resistant to mildew, blackspot and rust under normal growing conditions.

Response to climatic conditions: Strong resistance to rain and heat. Resistant to cold to −3° C.

I claim:

1. A new and distinct variety of petunia plant, substantially as herein shown and described, characterized particularly by its bright red, medium sized flowers and its profuse flowering, pendant vigorous habit and free branching.

* * * * *